US012661072B2

(12) United States Patent
    Kadrolkar et al.

(10) Patent No.: US 12,661,072 B2
(45) Date of Patent: Jun. 23, 2026

(54) HVAD ADVERSE EVENT DETECTION FROM CARDIAC COMPASS DATA

(71) Applicant: Boston Scientific Scimed, Inc., Maple Grove, MN (US)

(72) Inventors: Abhijit Kadrolkar, St. Paul, MN (US); Troy E. Jackson, Rogers, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 773 days.

(21) Appl. No.: 17/820,132

(22) Filed: Aug. 16, 2022

(65) Prior Publication Data

US 2023/0056430 A1 Feb. 23, 2023

Related U.S. Application Data

(60) Provisional application No. 63/233,814, filed on Aug. 17, 2021.

(51) Int. Cl.
    *A61B 5/00* (2006.01)
    *A61B 5/024* (2006.01)
    *G16H 40/67* (2018.01)
    *G16H 50/30* (2018.01)

(52) U.S. Cl.
    CPC ........ *A61B 5/7275* (2013.01); *A61B 5/02405* (2013.01); *G16H 40/67* (2018.01); *G16H 50/30* (2018.01)

(58) Field of Classification Search
    None
    See application file for complete search history.

(56) References Cited

U.S. PATENT DOCUMENTS

| | | | |
|---|---|---|---|
| 6,234,772 B1 | 5/2001 | Wampler et al. | |
| 8,512,013 B2 | 8/2013 | LaRose et al. | |
| 9,592,327 B2 * | 3/2017 | Wariar ................ | A61N 1/3702 |
| 10,159,775 B2 | 12/2018 | Voskoboynikov et al. | |
| 10,368,757 B2 | 8/2019 | Demou et al. | |
| 10,765,791 B2 | 9/2020 | Moyer et al. | |
| 2016/0354032 A1 * | 12/2016 | Wariar ................ | A61B 5/4875 |
| 2017/0095160 A1 * | 4/2017 | Thakur ................ | A61B 5/0535 |

(Continued)

OTHER PUBLICATIONS

International Search Report and Written Opinion of International Application No. PCT/US2022/075063 dated Jan. 3, 2023, 9 pp.

*Primary Examiner* — Mallika D Fairchild
(74) *Attorney, Agent, or Firm* — Seager Tufte & Wickhem, LLP

(57) ABSTRACT

An example system includes an implantable medical device configured to obtain measurement values of one or more patient metrics; and processing circuitry configured to: determine a baseline value for each of the respective one or more patient metrics based on measurement values of the one or more patient metrics over a first period of time; determine a short-term value for each of the one or more patient metrics based on measurement values of the one or more patient metrics over a second period of time, determine a difference between each of the short-term values and the respective baseline value for each of the one or more patient metrics; determine that a risk of an adverse event occurring in the patient is high in response to the determined difference meeting a respective adverse event risk threshold; and generate for output an adverse event high risk alert.

20 Claims, 7 Drawing Sheets

(56) References Cited

U.S. PATENT DOCUMENTS

| 2019/0282743 | A1 | 9/2019 | Agarwal et al. |
| 2020/0008686 | A1 | 1/2020 | Khair |
| 2020/0196944 | A1 | 6/2020 | Minor et al. |

* cited by examiner

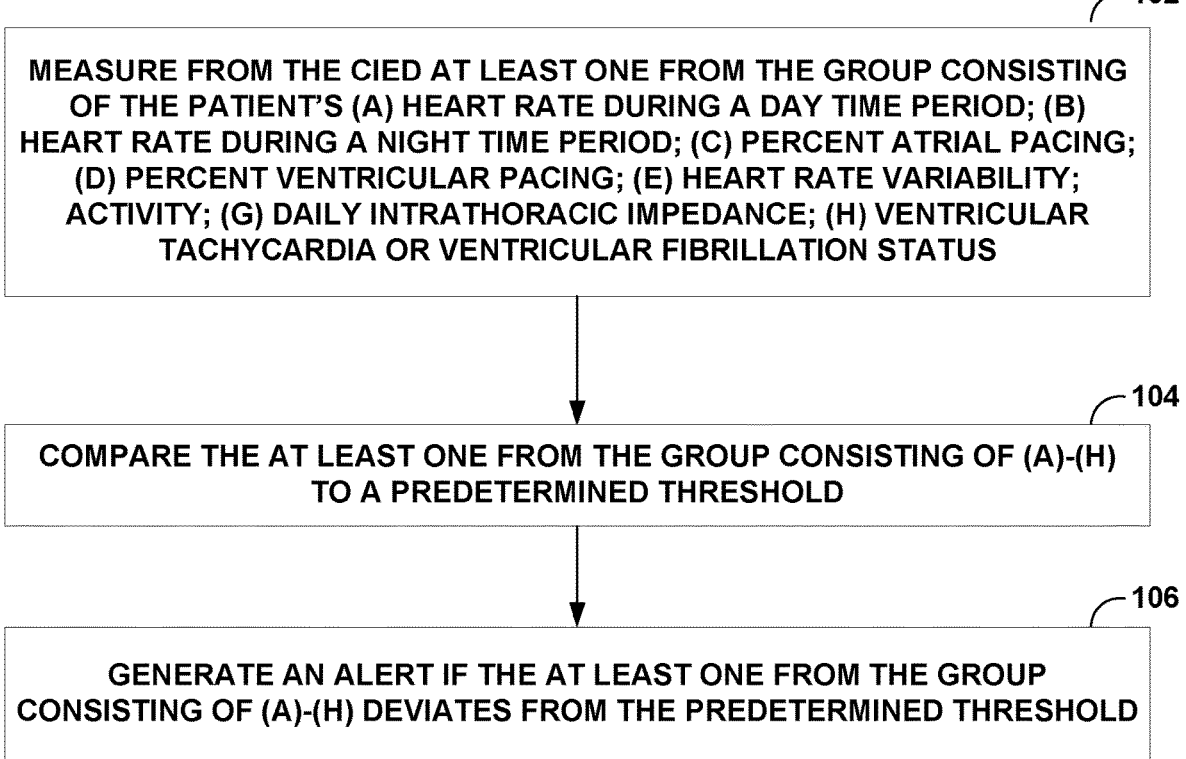

MEASURE FROM THE CIED AT LEAST ONE FROM THE GROUP CONSISTING OF THE PATIENT'S (A) HEART RATE DURING A DAY TIME PERIOD; (B) HEART RATE DURING A NIGHT TIME PERIOD; (C) PERCENT ATRIAL PACING; (D) PERCENT VENTRICULAR PACING; (E) HEART RATE VARIABILITY; ACTIVITY; (G) DAILY INTRATHORACIC IMPEDANCE; (H) VENTRICULAR TACHYCARDIA OR VENTRICULAR FIBRILLATION STATUS

COMPARE THE AT LEAST ONE FROM THE GROUP CONSISTING OF (A)-(H) TO A PREDETERMINED THRESHOLD

GENERATE AN ALERT IF THE AT LEAST ONE FROM THE GROUP CONSISTING OF (A)-(H) DEVIATES FROM THE PREDETERMINED THRESHOLD

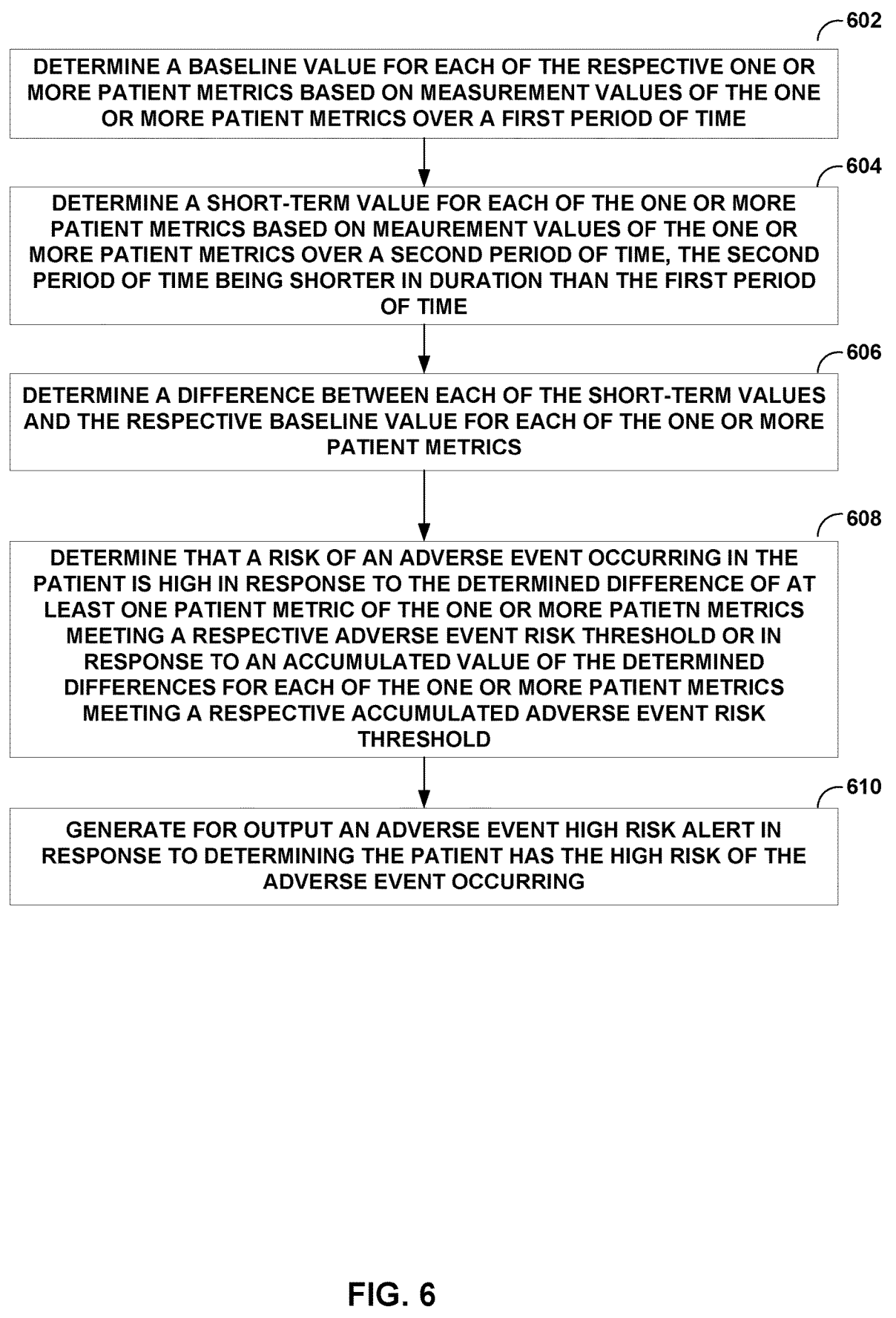

DETERMINE A BASELINE VALUE FOR EACH OF THE RESPECTIVE ONE OR MORE PATIENT METRICS BASED ON MEASUREMENT VALUES OF THE ONE OR MORE PATIENT METRICS OVER A FIRST PERIOD OF TIME

604

DETERMINE A SHORT-TERM VALUE FOR EACH OF THE ONE OR MORE PATIENT METRICS BASED ON MEAUREMENT VALUES OF THE ONE OR MORE PATIENT METRICS OVER A SECOND PERIOD OF TIME, THE SECOND PERIOD OF TIME BEING SHORTER IN DURATION THAN THE FIRST PERIOD OF TIME

606

DETERMINE A DIFFERENCE BETWEEN EACH OF THE SHORT-TERM VALUES AND THE RESPECTIVE BASELINE VALUE FOR EACH OF THE ONE OR MORE PATIENT METRICS

608

DETERMINE THAT A RISK OF AN ADVERSE EVENT OCCURRING IN THE PATIENT IS HIGH IN RESPONSE TO THE DETERMINED DIFFERENCE OF AT LEAST ONE PATIENT METRIC OF THE ONE OR MORE PATIETN METRICS MEETING A RESPECTIVE ADVERSE EVENT RISK THRESHOLD OR IN RESPONSE TO AN ACCUMULATED VALUE OF THE DETERMINED DIFFERENCES FOR EACH OF THE ONE OR MORE PATIENT METRICS MEETING A RESPECTIVE ACCUMULATED ADVERSE EVENT RISK THRESHOLD

610

GENERATE FOR OUTPUT AN ADVERSE EVENT HIGH RISK ALERT IN RESPONSE TO DETERMINING THE PATIENT HAS THE HIGH RISK OF THE ADVERSE EVENT OCCURRING

FIG. 6

HVAD ADVERSE EVENT DETECTION FROM CARDIAC COMPASS DATA

This application claims the benefit of U.S. Provisional Application Ser. No. 63/233,814 (filed Aug. 17, 2021), which is entitled "HVAD ADVERSE EVENT DETECTION FROM CARDIAC COMPASS DATA" and is incorporated by reference herein in its entirety.

FIELD

The present technology is generally related to method and system for detecting adverse events associated with an implantable blood pump in patients that also have a cardiac implanted electronic device (CIED).

BACKGROUND

Implantable blood pumps including heart ventricular assist devices (HVAD), and in particular, left ventricular assist devices (LVAD) have a high incidence of adverse events, such as thrombus, stroke, and ventricular arrythmia. Such adverse events are typically detected by analysis of on-device data, such as waveforms associated with operation of the implantable blood pump and analysis of log files. However, such detection methods often do not provide an early warning of upcoming adverse events.

Additionally, over 80% of patients with an LVAD also have a CIED, such as a pacing device, implantable cardioverter defibrillator (ICD), or cardiac resynchronization therapy (CRT) device. Such CIED devices typically monitor several variables associated with operation of the CIED.

SUMMARY

The techniques of this disclosure generally relate to method and system for determining that a risk of an adverse event occurring is high in a patient with an implantable blood pump and a cardiac implanted electronic device (CIED) and generating for output an adverse event high risk alert in response to determining the patient has the high risk of the adverse event occurring. In response to the generation of the adverse event high risk alert, the techniques and/or system may send a signal to one or more of a clinician computing device or an HVAD to perform a medical intervention to prevent or reduce the chances of a potential upcoming adverse event, such as an HVAD induced ventricular arrythmia, thrombus, stroke, or ventricular arrythmia, from occurring or continuing to occur, which may prevent or reduce damage to the heart of the patient and/or prevent or reduce harm to the patient.

In one aspect, the present disclosure provides a system comprising an implantable medical device configured to obtain measurement values of one or more patient metrics of a patient; and processing circuitry configured to: determine a baseline value for each of the respective one or more patient metrics based on measurement values of the one or more patient metrics over a first period of time; determine a short-term value for each of the one or more patient metrics based on measurement values of the one or more patient metrics over a second period of time, the second period of time being shorter in duration than the first period of time; determine a difference between each of the short-term values and the respective baseline value for each of the one or more patient metrics; determine that a risk of an adverse event occurring in the patient is high in response to the determined difference of at least one patient metric of the one or more patient metrics meeting a respective adverse event risk threshold or in response to an accumulated value of the determined differences for each of the one or more patient metrics meeting a respective accumulated adverse event risk threshold; and generate for output an adverse event high risk alert in response to determining the patient has the high risk of the adverse event occurring.

In one aspect, the present disclosure provides a method of obtaining one or more measurement values of one or more patient metrics of a patient; determining a baseline value for each of the respective one or more patient metrics based on measurement values of the one or more patient metrics over a first period of time; determining a short-term value for each of the one or more patient metrics based on measurement values of the one or more patient metrics over a second period of time, the second period of time being shorter than the first period of time; determining a difference between each of the short-term values and the respective baseline value for each of the one or more patient metrics; determining that a risk of an adverse event occurring in the patient is high in response to the determined difference of at least one patient metric of the one or more patient metrics meeting a respective adverse event risk threshold or in response to an accumulated value of the determined differences for each of the one or more metrics meeting a respective accumulated adverse event risk threshold; and generating for output an adverse event high risk alert in response to determining the patient has the high risk of the adverse event occurring.

In one aspect, the present disclosure provides a method for detecting adverse events associated with an implantable blood pump in patients that also have a cardiac implanted electronic device (CIED) the method includes measuring from the CIED at least one of the patient's (a) heart rate during a day time period; (b) heart rate during a night time period; (c) percent atrial pacing; (d) percent ventricular pacing; (e) heart rate variability; (f) activity; (g) daily intrathoracic impedance; and (h) ventricular tachycardia or ventricular fibrillation status. The at least one of (a)-(h) is compared to a predetermined threshold and an alert is generated if the at least one of (a)-(h) deviates from the predetermined threshold.

In one aspect, a system for detecting adverse events in a patient with an implantable blood pump and with a cardiac implanted electronic device (CIED), the system includes a controller in communication with the CIED, the controller including processing circuitry configured to measure from the CIED at least one of the patient's (a) heart rate during a day time period; (b) heart rate during a night time period; (c) percent atrial pacing; (d) percent ventricular pacing; (e) heart rate variability; (f) activity; (g) daily intrathoracic impedance; and (h) ventricular tachycardia or ventricular fibrillation status. The at least one of (a)-(h) is compared to a predetermined threshold. An alert is generated if the at least one of (a)-(h) deviates from the predetermined threshold.

In one aspect, a method of detecting thrombus in a patient with an implantable blood pump and with a cardiac implanted electronic device (CIED) includes measuring from the CIED, the patient's (a) heart rate during a day time period; (b) heart rate during a night time period; (c) percent atrial pacing; (d) percent ventricular pacing; (e) heart rate variability; (f) activity; (g) daily intrathoracic impedance; and (h) ventricular tachycardia or ventricular fibrillation status; (a)-(h) is compared to a predetermined threshold. An alert is generated if (a)-(h) deviates from the predetermined threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is a flow chart showing example techniques for detecting adverse events in a patient with an implantable blood pump and with a cardiac implanted electronic device (CIED).

FIG. 6 is a flow chart showing example techniques for generating an adverse event high risk alert, in accordance with techniques described herein.

DETAILED DESCRIPTION

Over 80% of patients with an HVAD, in particular an LVAD, also have an implantable medical device, such as a CIED. Patients with an HVAD, in particular LVAD, have a high incidence of adverse events, such as HVAD induced ventricular arrythmia, thrombus, stroke, and ventricular arrythmia. In some examples, if adverse events are not detected early, significant harm, even death, may happen to a patient.

In accordance with techniques of this disclosure, a system or method may determine that a risk of an adverse event occurring is high in a patient and generate for output an adverse event high risk alert in response to determining the patient has the high risk of the adverse event occurring. The early detection and output of the adverse event high risk alert may trigger a medical intervention to be performed to prevent or reduce the chances of the identified adverse event, such as an HVAD induced ventricular arrythmia, thrombus, stroke, or ventricular arrythmia, from occurring or continuing to occur. This may prevent or reduce damage to the heart of the patient and/or prevent or reduce harm to the patient.

Figure 1:
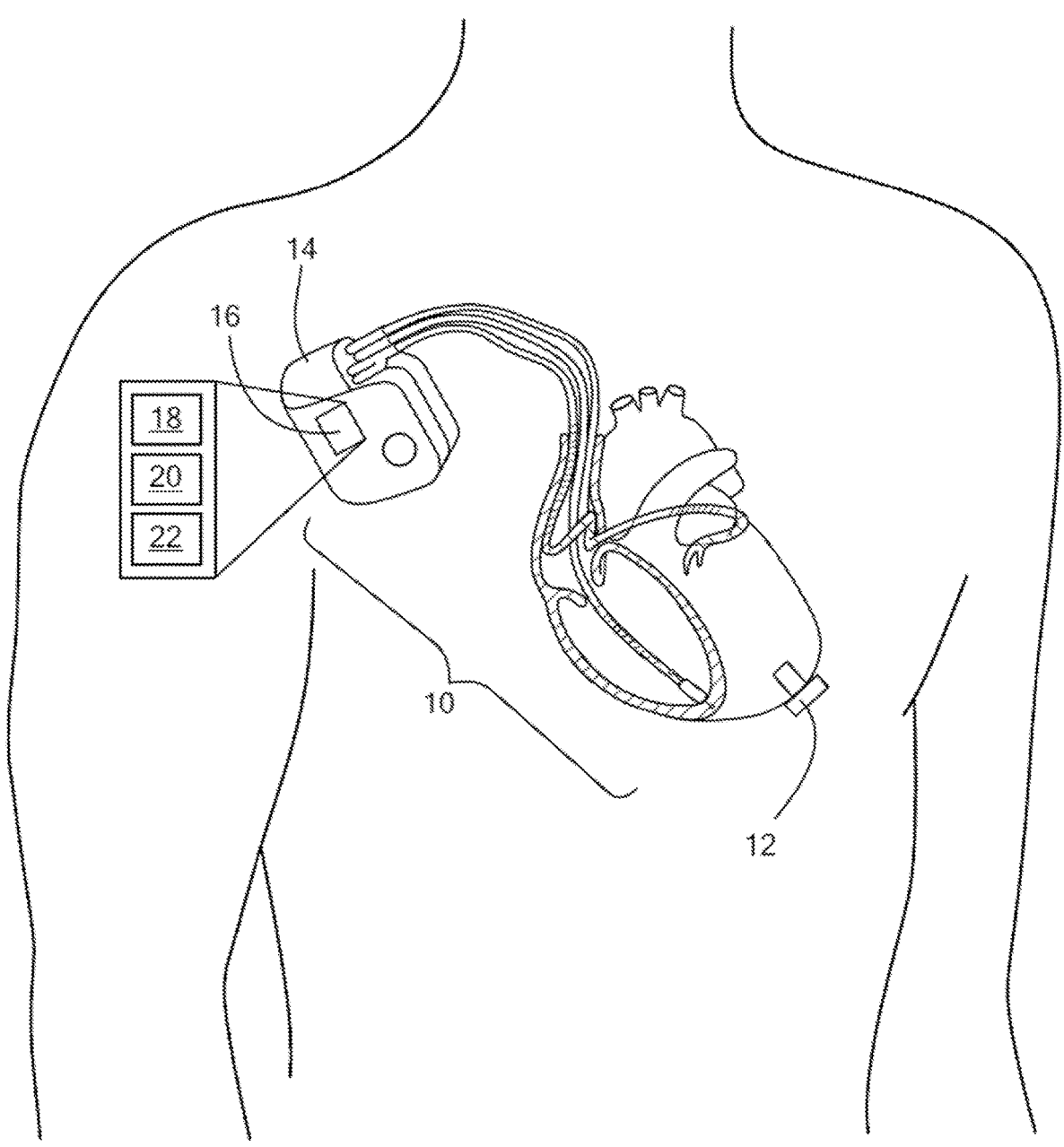
FIG. 1 is an example system view showing an implanted blood pump and a cardiac implanted electronic device.

Referring now to the drawings in which like reference designators refer to like elements. FIG. 1 is a system view showing an implanted blood pump and a cardiac implanted electronic device. In FIG. 1, an exemplary medical system is shown that is typically associated within patients having both an implantable blood pump and a CIED and designated generally as "10." The system 10 may include an implantable blood pump 12 such as the HVAD™ manufactured by HeartWare, Inc. configured to assist the heart in pumping blood throughout the body. The HVAD™ is further described in U.S. Pat. Nos. 6,234,772 and 8,512,013, the disclosures of which are incorporated by reference. The pump 12 may be, for example, a left or right ventricular assist device, and other blood pumps 12 are contemplated by this disclosure. The system 10 may further include a CIED 14, for example, an implantable cardiac monitor (ICM) to obtain measurement values of one or more patient metrics, a pacing device, a cardiac resynchronization therapy (CRT) device, or an implantable cardioverter-defibrillator (ICD) in electrical communication with the heart to provide therapy, such as rhythm therapy, to the heart. In some examples, CIED 14 may be referred to as an implantable medical device (IMD). The CIED 14 may include an on-board controller 16 configured to control operations of the CIED 14 and further includes processing circuitry 18 having a memory 20 and CPU 22 configured to process, record, and monitor the various functions of the CIED. In configurations, the CIED 14 is in communication with a remote controller (not shown) configured to analyze and process the various data recorded by the CIED 14.

In some examples, system 10 may include an implantable medical device, such as CIED 14 and processing circuitry 18. An IMD, such as CIED 14, may be configured to obtain measurement values of one or more patient metrics of a patient. The one or more patient metrics may include at least one of (a) heart rate during a daytime period; (b) heart rate during a nighttime period; (c) percent atrial pacing; (d) percent ventricular pacing; (e) heart rate variability; (f) activity; (g) daily intrathoracic impedance; or (h) ventricular tachycardia or ventricular fibrillation status. Although not illustrated in FIG. 1, implantable medical device, such as CIED 14, may include electrode(s) and other sensor(s) to sense physiological signals indicative of patient metrics of a patient, and may collect and store sensed patient metrics based on the signals.

Processing circuitry 18 may be configured to determine a baseline value for each of the respective one or more patient metrics based on measurement values of the one or more patient metrics over a first period of time. Processing circuitry 18 may further be configured to determine a short-term value for each of the one or more patient metrics based on measurement values of the one or more patient metrics over a second period of time, the second period of time being shorter in duration than the first period of time.

Processing circuitry 18 may further be configured to determine a difference between each of the short-term values to the respective baseline value for each of the one or more patient metrics. Processing circuitry 18 may further be configured to determine that a risk of an adverse event occurring in the patient is high in response to the determined difference of at least one patient metric of the one or more patient metrics meeting a respective adverse event risk threshold or in response to an accumulated value of the determined differences for each of the one or more patient metrics meeting a respective accumulated adverse event risk threshold.

Processing circuitry 18 may further be configured generate for output an adverse event high risk alert in response to determining the patient has the high risk of the adverse event occurring. The generated adverse event high risk alert may cause a medical intervention to be performed on the patient, such as adjusting an HVAD parameter, adjusting medication, performing surgery, or other types of medical interventions to prevent or reduce the chances of a potential upcoming adverse event, such as a thrombus, stroke, HVAD induced arrythmia, or ventricular arrythmia, from occurring.

In some examples, processing circuitry 18 may further be configured to apply a long-term filter to the measurement values of each of the one or more patient metrics over the first period of time to determine the baseline value for each of the respective one or more patient metrics. In some examples, processing circuitry 18 may further be configured to apply a short-term filter to the measurement values of each of the one or more patient metrics over the second period of time to determine the short-term value for each of the respective one or more patient metrics.

In some examples, when the adverse event is a thrombus, processing circuitry 18 may further be configured to determine a risk of the thrombus occurring in the patient to be high based on the determined difference of at least one patient metric of patient metrics (a)-(g) meeting a respective thrombus risk threshold or based on an accumulated value of the determined differences for each of the patient metrics (a)-(g) meeting a respective accumulated thrombus risk threshold.

In some examples, when the adverse event is a stroke, processing circuitry 18 may further be configured to determine a risk of the stroke occurring in the patient to be high based on the determined difference of at least one patient metric of patient metrics (a)-(e) meeting a respective stroke risk threshold or based on an accumulated value of the determined differences for each of the patient metrics (a)-(e) meeting a respective accumulated stroke risk threshold.

In some examples, when the adverse event is an HVAD induced ventricular arrythmia, processing circuitry 18 may further be configured to determine a risk of the HVAD induced ventricular arrythmia occurring in the patient to be high based on the determined difference of patient metric (h) meeting a respective HVAD induced ventricular arrythmia risk threshold.

FIG. 2 is a flow chart showing example techniques for detecting adverse events in a patient with an implantable blood pump and with a cardiac implanted electronic device (CIED). The techniques of FIG. 2, which may be carried out by processing circuitry 18 or by the remote controller, includes measuring from the CIED 14 a variety of different patient metrics, such as cardiovascular parameters. These cardiovascular parameters that are being measured may include the patient's (a) heart rate during a day time period; (b) heart rate during a night time period; (c) percent atrial pacing; (d) percent ventricular pacing; (e) heart rate variability; (f) activity; (g) daily intrathoracic impedance; and (h) ventricular tachycardia or ventricular fibrillation status (102). In particular, one or more of (a)-(h) may be measured from a patient with a CIED to provide an early warning as to the potential for thrombus, stroke, or ventricular arrythmia in patients with an implantable blood pump 12. In some examples, percent atrial pacing may correspond to a percentage amount an atrium of a heart is being paced over a period of time. In some examples, percent ventricular pacing may correspond to a percentage amount one or more of the left and/or right ventricles of a heart are being paced over a period of time. In some examples, the ventricular arrythmia may be an LVAD induced arrythmia, which may be at least partially caused by suction of a heart wall against the inlet of the LVAD that may cause certain rhythms or cadences that lead to the ventricular arrythmia. Having early warning information about potential cardiac events may allow for earlier interventions and/or prevent further damage to the LVAD or the patient's heart. In the example of detecting a thrombus, (a)-(g) are used in the method, in detecting stroke (a)-(e) are used in the method, and in detecting ventricular arrythmia only (h) is used in the method.

The at least one of (a)-(h) is compared to a threshold (104). In some examples, the threshold may be a metric-specific threshold. In some examples, the threshold may be predetermined. In some examples, a predetermined threshold may be based on HVAD patients. In some examples, the threshold may be a comprehensive threshold to be compared to a plurality of respective metrics being combined. The predetermined threshold may be stored in, for example, a predetermined table or chart in the memory 20 and may be preprogrammed into the memory 20 and may further be updateable. For example, the at least one of (a)-(h) may be a long-term filter to establish a respective baseline of the at least one of (a)-(h). The respective baselines may be patient-specific. In some non-limiting examples, a duration of a long-term filter may be for 3-months, 6-months, 9-months, 1-year, 18-months, 2-years, or 5-years. Moreover, the at least one of (a)-(h) may be filtered against a short-term filter to establish a short-term trend of the at least one of (a)-(h). In some non-limiting examples, a duration of a short-term filter may be for 5-days, 10-days, 20-days, 30-days, 45-days, 60-days, or 75-days. In some examples, a duration of a short-term filter is less than a duration of a long-term filter. The long-term filtered at least one of (a)-(h) is subtracted from the short-term filtered at least one of (a)-(h) to determine deviations from the respective established baseline. That is, the difference between the long-term filtered data and the short-term filtered data provides a quantitative measure of a patient-specific deviation from the baseline that may be associated with an adverse event, such as a presence of a thrombus in the HVAD, a suction condition of the HVAD, a stroke, or an arrythmia. The determined deviations from the established respective baseline are compared for each of the least one of (a)-(h) to a respective interim threshold to determine respective interim events.

In some examples, a baseline value for each of a respective one or more patient metrics may be determined based on measurement values of the one or more patient metrics over a first period of time, and a short-term value for each of the one or more patient metrics may be determined based on measurement values of the one or more patient metrics over a second period of time, the second period of time being shorter in duration than the first period of time. In some examples, a difference may be determined between each of the short-term values to the respective baseline value for each of the one or more patient metrics. In some examples, a risk of an adverse event occurring in the patient may be determined to be high in response to the determined difference of at least one patient metric of the one or more patient metrics meeting a respective adverse event risk threshold or in response to an accumulated value of the determined differences for each of the one or more patient metrics meeting a respective accumulated adverse event risk threshold. An adverse event high risk alert may then be generated for output in response to determining the patient has the high risk of the adverse event occurring.

In some examples, when the adverse event is a thrombus, a risk of the thrombus occurring in the patient may be determined to be high based on the determined difference of at least one patient metric of patient metrics (a)-(g) meeting a respective thrombus risk threshold or based on an accumulated value of the determined differences for each of the patient metrics (a)-(g) meeting a respective accumulated thrombus risk threshold.

In some examples, when the adverse event is a stroke, a risk of the stroke occurring in the patient may be determined to be high based on the determined difference of at least one patient metric of patient metrics (a)-(e) meeting a respective stroke risk threshold or based on an accumulated value of the determined differences for each of the patient metrics (a)-(e) meeting a respective accumulated stroke risk threshold.

In some examples, when the adverse event is an HVAD induced ventricular arrythmia, a risk of the HVAD induced ventricular arrythmia occurring in the patient may be determined to be high based on the determined difference of patient metric (h) meeting a respective HVAD induced ventricular arrythmia risk threshold.

In some examples, meeting a respective threshold may include being above the respective threshold, being equal to or above the respective threshold, being equal to the respective threshold, being equal to or below the respective threshold, or being below the respective threshold.

In the example of thrombus detection, for heart rate and pacing status, both positive and negative deviations (from the baseline) are used to update short-term and long-term filter estimates, which are subsequently provided to respective accumulators, while for heart rate variability, activity and thoracic impedance only negative deviations are utilized. An integrator is used to accumulate differences between the filter estimates over a moving time-window, and a threshold on the accumulated differences is used to trigger an interim event. These interim threshold crossings are subsequently passed to a fusion module that collects threshold crossings across all input variables. A predetermined threshold, based on the time-averaged mean of all collected interim events, is used to trigger an alarm condition. In particular, the respective interim events are summed over a predetermined period of time, for example, 14 days to 6 months, and the summed respective interim events are compared to the predetermined threshold. If the at least one of (a)-(h) deviates from the predetermined threshold an adverse event high risk alert may be generated by the processing circuitry (106).

In some examples, the adverse event high risk alert generated by the processing circuitry may be output to another device, such as a clinician computing device, either directly or via an intermediary computing device(s). The adverse event high risk alert may cause a signal to be sent to a clinician computing device to indicate to or instruct a clinician to perform a medical intervention, such as adjusting a HVAD parameter, adjusting medication, performing surgery, or other types of medical interventions to prevent or reduce the chances of a potential upcoming adverse event, such as a thrombus, stroke, or ventricular arrythmia, from occurring. In some examples, the processing circuitry may cause a signal to be sent to an HVAD to perform a medical intervention, such as adjusting an HVAD parameter in response to generating an adverse event high risk alert to prevent or reduce the chances of a potential upcoming adverse event, such as an HVAD induced ventricular arrythmia, LVAD induced arrythmia, thrombus, stroke, or ventricular arrythmia, from occurring. In this manner, the techniques of this disclosure may effect a particular treatment or prophylaxis for a disease or medical condition.

Figure 3:
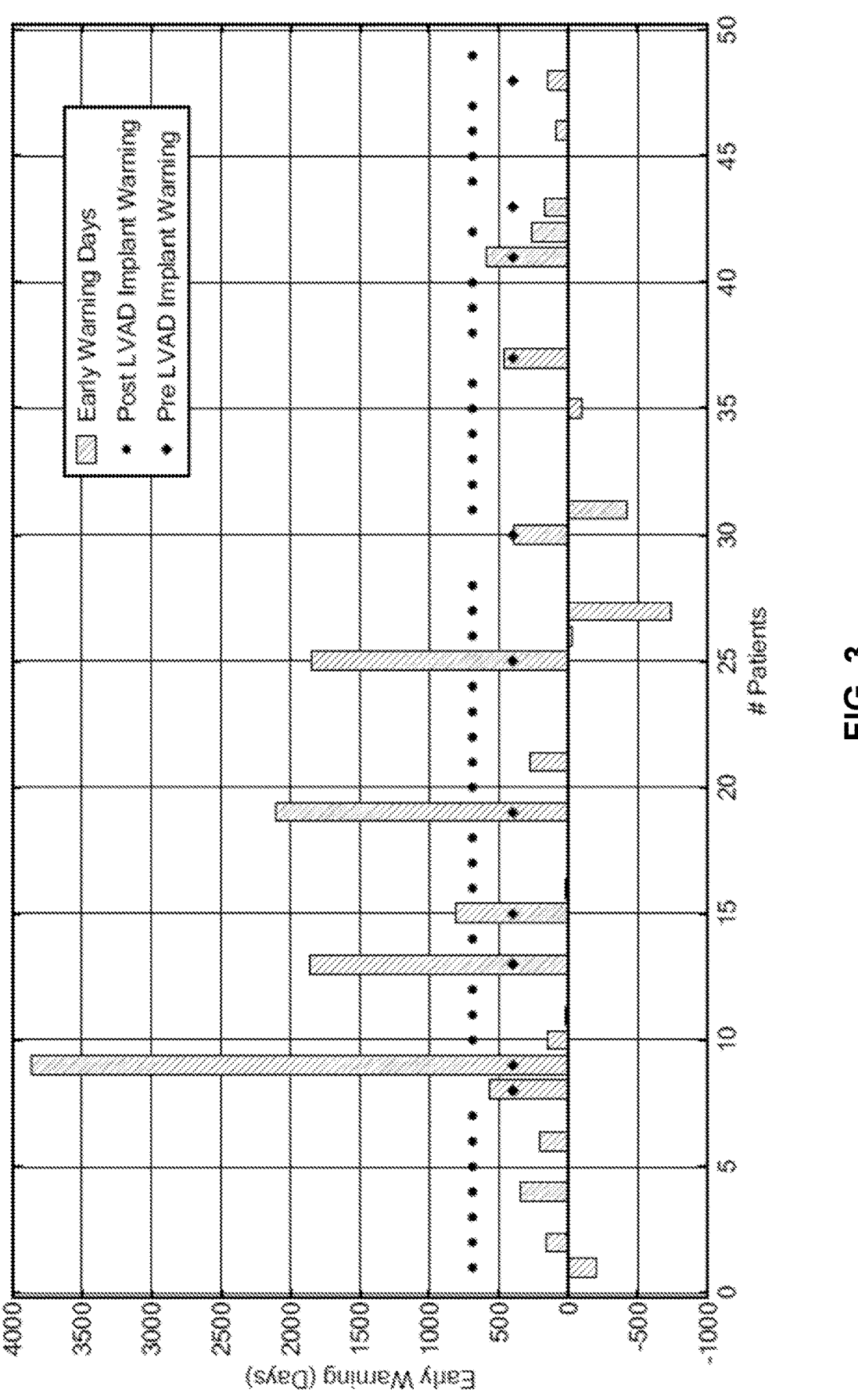
FIG. 3 is a chart showing the early detecting of thrombus using the techniques shown in FIG. 2.

FIG. 3 is a chart showing the early detecting of thrombus using the techniques shown in FIG. 2. As shown in FIG. 3, the algorithm for detecting thrombus was evaluated on a dataset of 49 patient data streams. Early detection of thrombus was triggered in 19 out of 49 cases. In 11 cases, the alert was observed before the date of LVAD implantation and in 8 cases, the alert was observed after the date of LVAD implantation. The average early warning of thrombus detection for post-LVAD implantation alert trigger was 7 days.

Figure 4:
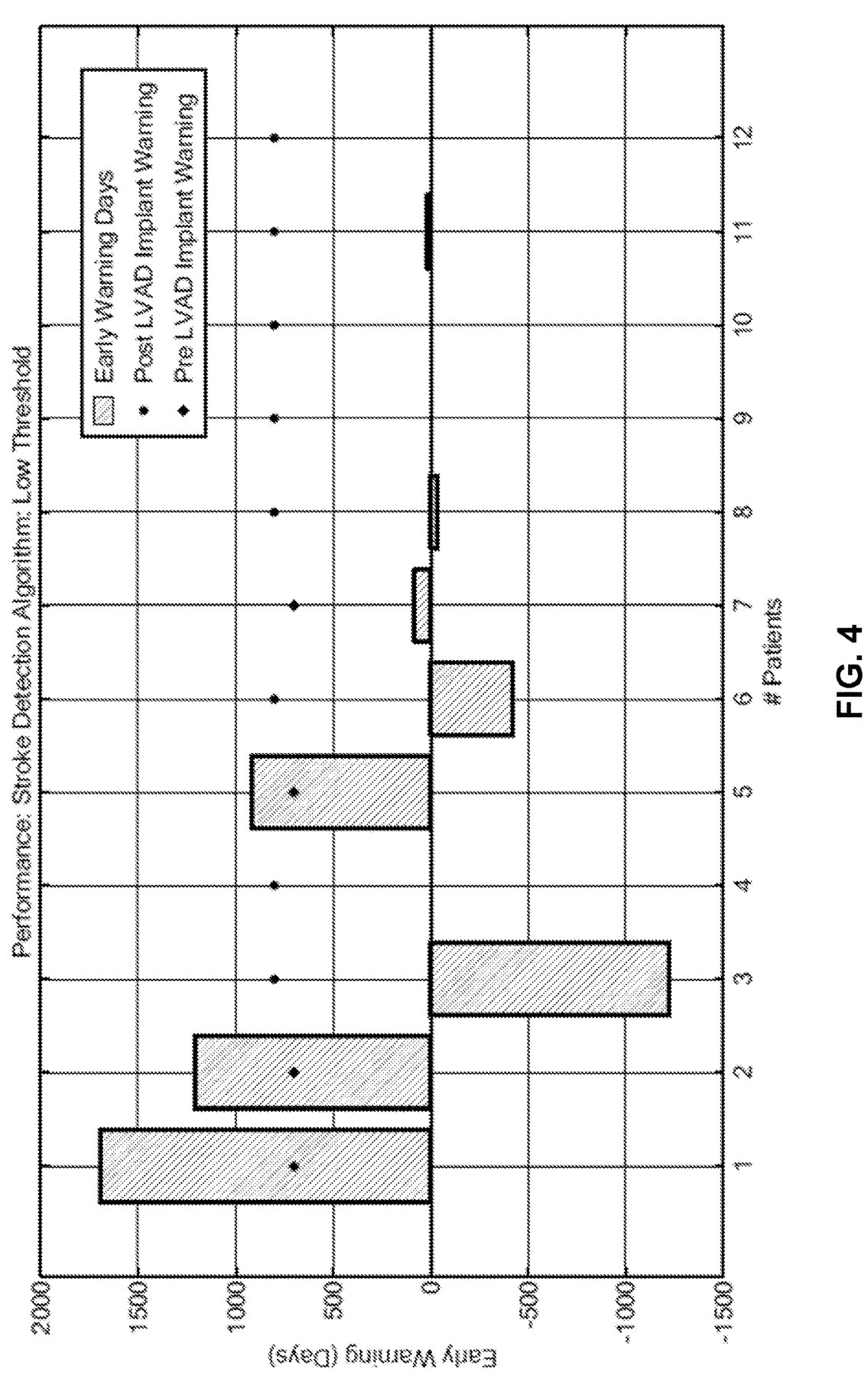
FIG. 4 is a chart showing the early detecting of stroke using the techniques shown in FIG. 2.

FIG. 4 is a chart showing the early detecting of stroke using the techniques shown in FIG. 2. Referring now to FIG. 4, similar to the thrombus detection algorithm discussed in the last section, the stroke detection algorithm uses heart rate, pacing status, heart rate variability and activity as inputs, and monitors the inputs for deviations from a stable operating state. This monitoring is achieved by implementing a pair of averaging filters a short duration, for example 30 days, and a long duration filter, for example, 6-months, on each of the inputs, in the same manner as was achieved for the thrombus algorithm. The long duration filter estimates a patient-specific baseline for each input, and the difference between the short duration and long duration filters provides a quantitative measure of patient-specific deviation from baseline that may be associated with a stroke event. For heart rate and pacing status, both positive and negative deviations are provided to the respective accumulators, while for heart rate variability and activity only negative deviations are utilized. And, same as for thrombus, an integrator is used to accumulate differences between the filter estimates over a moving time-window, and a threshold on the accumulated differences is used to trigger an interim event. These interim threshold crossings are subsequently passed to a fusion module that collects threshold crossings across all input variables. A predetermined threshold, on the time-averaged mean of all collected interim events, is used to trigger an alert condition. As shown in FIG. 4, the stroke detection algorithm was evaluated on a dataset of 12 patient data streams, and it can be seen that detection was triggered in 4 out of 12 cases. In 3 cases, an alert trigger was observed before date of LVAD implant.

Figure 5:
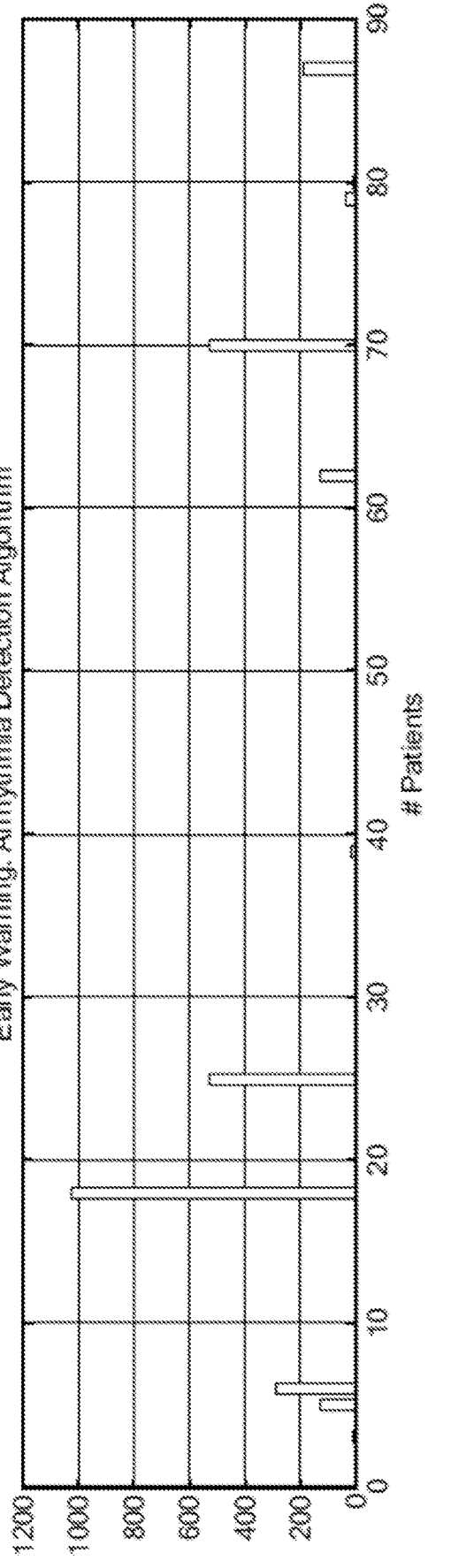
FIG. 5 is a chart showing the early detecting of ventricular tachycardia using the techniques shown in FIG. 2.

FIG. 5 is a chart showing the early detecting of ventricular tachycardia using the techniques shown in FIG. 2. Referring now to FIG. 5, to capture sudden onset of arrythmia and build-up of prolonged time in arrythmia, a single variable algorithm is utilized to detect HVAD induced arrythmia, such as LVAD induced arrythmia. In some examples, LVAD induced arrythmia may be a particular type of HVAD induced arrythmia. In some examples, an HVAD induced arrythmia may be at least partially caused by a suction condition, in which a ventricle may collapse in such a way that a heart wall occludes the inlet of the HVAD, which can cause the flow rate through the HVAD to decline and lead to inadequate blood perfusion. The suction condition may cause certain cardiac rhythms or cadences that lead to an arrythmia. In some examples, an HVAD induced arrythmia, such as an LVAD induced arrythmia, may have a higher burden rate than a naturally occurring arrythmia. Accordingly, a VT count threshold for an HVAD induced arrythmia may be greater than a VT count threshold for a naturally occurring arrythmia. For example, if the ventricular tachycardia (VT) count crosses an HVAD induced threshold, for example, a count of 3, at any point of time, a detection alert of an HVAD induced arrythmia may be triggered. Additionally, a detection alert may also be triggered if the VT count is greater than one for two consecutive days or greater than one for 5 days over a 7-day period.

This algorithm was tested on available data, and while detection was triggered in all of the arrhythmia cases, early detection was triggered in 14 out of 89 cases.

Figure 7:
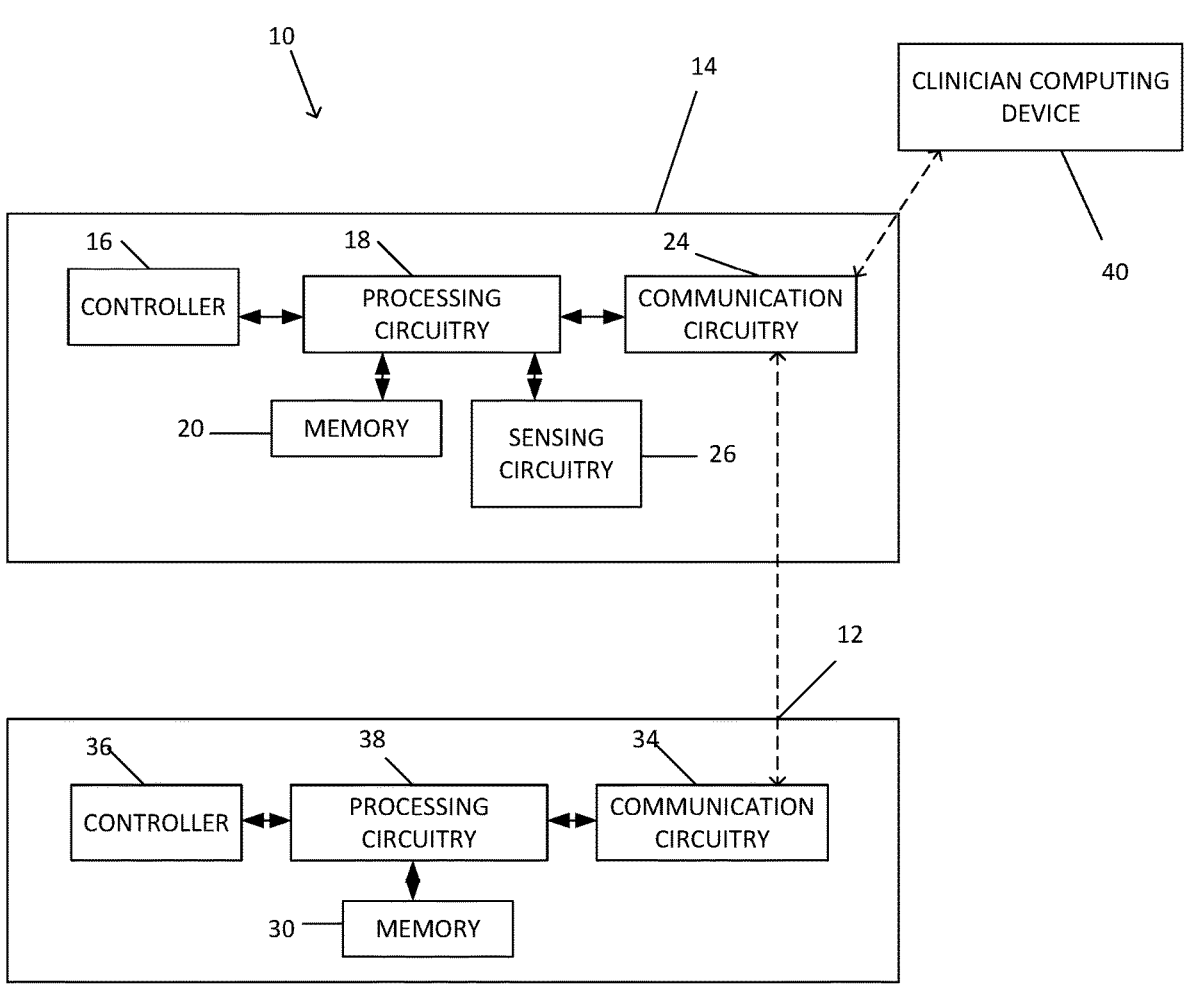
FIG. 7 is a functional block diagram of an example configuration of electronic components of an example system, in accordance with techniques described herein.

FIG. 6 is a flow diagram illustrating an example technique of generating an adverse event high risk alert in accordance with a system 10, as shown in FIG. 7. In some examples, processing circuitry 18 of CIED 14 may be configured to determine a baseline value for each of the respective one or more patient metrics based on measurement values of the one or more patient metrics over a first period of time (602). For example, processing circuitry 18 may determine a baseline value for one or more of heart rate during a day time period, heart rate during a night time period, percent atrial pacing, percent ventricular pacing, heart rate variability, activity, daily intrathoracic impedance, or ventricular tachycardia or ventricular fibrillation over a period of time. In some examples, processing circuitry 18 may be configured to determine a short-term value for each of the one or more patient metrics based on measurement values of the one or more patient metrics over a second period of time, the second period of time being shorter in duration than the first period of time (604). For example, processing circuitry 18 may determine a short-term value for one or more of heart rate during a day time period, heart rate during a night time period, percent atrial pacing, percent ventricular pacing, heart rate variability, activity, daily intrathoracic impedance, or ventricular tachycardia or ventricular fibrillation over a period of time shorter than the baseline value is determined. In some examples, processing circuitry 18 may be configured to determine a difference between each of the short-term values and the respective baseline value for each of the one or more patient metrics (606). For example, processing circuitry 18 may determine a difference between the short-term value and the baseline value for each of one or more of heart rate during a day time period, heart rate during a night time period, percent atrial pacing, percent ventricular pacing, heart rate variability, activity, daily intrathoracic impedance, or ventricular tachycardia or ventricular fibrillation. In some examples, processing circuitry 18 may be configured to determine that a risk of an adverse event occurring in the patient is high in response to the determined difference of at least one patient metric of the one or more patient metrics meeting a respective adverse event risk threshold or in response to an accumulated value of the determined differences for each of the one or more patient metrics meeting a respective accumulated adverse event risk threshold (608). For example, processing circuitry 18 may determine a risk of an adverse event, such as such as an HVAD induced ventricular arrythmia, LVAD induced arrythmia, thrombus, stroke, or ventricular arrythmia, is high in response to at least one of the determined difference between the short-term value and the baseline value of one or more of heart rate during a day time period, heart rate during a night time period, percent atrial pacing, percent ventricular pacing, heart rate variability, activity, daily intrathoracic impedance, or ventricular tachycardia or ventricular fibrillation meeting a respective adverse event risk threshold. Processing circuitry 18 may determine a risk of an adverse event, such as such as an HVAD induced ventricular arrythmia, LVAD induced arrythmia, thrombus, stroke, or ventricular arrythmia, is high in response to an accumulated value of the determined differences between the short-term value and the baseline value for each of one or more of heart rate during a day time period, heart rate during a night time period, percent atrial pacing, percent ventricular pacing, heart rate variability, activity, daily intrathoracic impedance, or ventricular tachycardia or ventricular fibrillation meeting a respective accumulated adverse event risk threshold. In some examples, processing circuitry 18 may be configured to generate for output an adverse event high risk alert in response to determining the patient has the high risk of the adverse event occurring (610). For example, processing circuitry 18 may output an adverse high risk alert to cause a medical intervention to be performed on the patient, such as adjusting an HVAD parameter, adjusting medication, performing surgery, or other types of medical interventions to prevent or reduce the chances of a potential upcoming adverse event, such as a thrombus, stroke, HVAD induced arrythmia, or ventricular arrythmia, from occurring.

In some examples, the one or more patient metrics comprise at least one of (a) heart rate during a day time period; (b) heart rate during a night time period; (c) percent atrial pacing; (d) percent ventricular pacing; (e) heart rate variability; (f) activity; (g) daily intrathoracic impedance; or (h) ventricular tachycardia or ventricular fibrillation status.

In some examples, processing circuitry 18 may apply a long-term filter to the measurement values of each of the one or more patient metrics over the first period of time to determine the baseline value for each of the respective one or more patient metrics. In some examples, processing circuitry 18 may apply a short-term filter to the measurement values of each of the one or more patient metrics over the second period of time to determine the short-term value for each of the respective one or more patient metrics.

FIG. 7 is a functional block diagram of an example configuration of electronic components of an example system 10. In some examples, sensing circuitry 26 may obtain measurement values of one or more patient metrics of a patient. In some examples, communication circuitry 24 may be configured to output a signal to another device in response to processing circuitry 18 generating an adverse event high risk alert, as discussed above. In some examples, the signal may cause another device, such as a clinician computing device 40, to indicate a patient is at a high risk of having an adverse event, such as such as an HVAD induced ventricular arrythmia, LVAD induced arrythmia, thrombus, stroke, or ventricular arrythmia, occur. In some examples, the signal may cause another device to indicate or instruct to a clinician to perform a medical intervention, such as adjusting an HVAD parameter, adjusting medication, performing surgery, or other types of medical interventions to prevent or reduce the chances of the adverse event, such as HVAD induced ventricular arrythmia, LVAD induced arrythmia, thrombus, stroke, or ventricular arrythmia, from occurring.

In some examples, in response to processing circuitry 18 generating an adverse event high risk alert, processing circuitry 18 may cause a signal to be sent, via communication circuitry 24, to communication circuitry 34 of a blood pump 12 to cause processing circuitry 38 of blood pump 12 to perform a medical intervention, such as adjusting an HVAD parameter, to prevent or reduce the chances of the potential upcoming adverse event, such as HVAD induced ventricular arrythmia, thrombus, stroke, or ventricular arrythmia, from occurring. In some examples, adjusting an HVAD parameter, such as by a clinician or by the blood pump 12 in response to receiving a signal from CIED 14, may include adjusting a rotational speed of a rotor of the blood pump 12.

In some examples where the adverse event is an HVAD induced ventricular arrythmia, in response to determining the patient has a high risk of an HVAD induced ventricular arrythmia occurring, processing circuitry 18 generates an adverse event high risk alert to cause a signal to be sent to one of a clinician computing device 40 or the HVAD 12 itself to cause adjustment of a rotational speed of a rotor of the blood pump 12 to stop the suction condition that causes the HVAD induced ventricular arrythmia from continuing to occur, which may prevent damage to the heart of the patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The following examples are a non-limiting list of clauses in accordance with one or more techniques of this disclosure.

Example 1: A system includes an implantable medical device configured to obtain measurement values of one or more patient metrics of a patient; and processing circuitry configured to: determine a baseline value for each of the respective one or more patient metrics based on measurement values of the one or more patient metrics over a first period of time; determine a short-term value for each of the one or more patient metrics based on measurement values of the one or more patient metrics over a second period of time, the second period of time being shorter in duration than the first period of time; determine a difference between each of the short-term values and the respective baseline value for each of the one or more patient metrics; determine that a risk of an adverse event occurring in the patient is high in response to the determined difference of at least one patient metric of the one or more patient metrics meeting a respective adverse event risk threshold or in response to an accumulated value of the determined differences for each of the one or more patient metrics meeting a respective accumulated adverse event risk threshold; and generate for output an adverse event high risk alert in response to determining the patient has the high risk of the adverse event occurring.

Example 2: The system of example 1, wherein the one or more patient metrics comprise at least one of (a) heart rate during a day time period; (b) heart rate during a night time period; (c) percent atrial pacing; (d) percent ventricular pacing; (e) heart rate variability; (f) activity; (g) daily intrathoracic impedance; or (h) ventricular tachycardia or ventricular fibrillation status.

Example 3: The system of example 2, wherein the processing circuitry is further configured to apply a long-term filter to the measurement values of each of the one or more patient metrics over the first period of time to determine the baseline value for each of the respective one or more patient metrics.

Example 4: The system of example 3, wherein the processing circuitry is further configured to apply a short-term filter to the measurement values of each of the one or more patient metrics over the second period of time to determine the short-term value for each of the respective one or more patient metrics.

Example 5: The system of example 4, wherein the first period of time is 6 months, and the second period of time is 30 days.

Example 6: The method of any of examples 4 and 5, wherein the long-term filter is a moving average filter applied over the first period of time.

Example 7: The system of any of examples 4 through 6, wherein the short-term filter is a moving average filter applied over the second period of time.

Example 8: The system of any of examples 1 through 7, wherein the adverse event is a heart ventricular assist device (HVAD) induced ventricular arrythmia.

Example 9: The system of any of examples 1 through 8, wherein the generated adverse event high risk alert is to cause a medical intervention to be performed on the patient.

Example 10: The system of any of examples 2 through 9, wherein the adverse event is a thrombus and the processing circuitry is further configured to determine a risk of the thrombus occurring in the patient is high in response to the determined difference of at least one patient metric of patient metrics (a)-(g) meeting a respective thrombus risk threshold or in response to an accumulated value of the determined differences for each of the patient metrics (a)-(g) meeting a respective accumulated thrombus risk threshold.

Example 11: The system of any of examples 2 through 10, wherein the adverse event is a stroke and the processing circuitry is further configured to determine a risk of the stroke occurring in the patient is high in response to the determined difference of at least one patient metric of patient metrics (a)-(e) meeting a respective stroke risk threshold or in response to an accumulated value of the determined differences for each of the patient metrics (a)-(e) meeting a respective accumulated stroke risk threshold.

Example 12: The system of any of examples 2 through 11, wherein the adverse event is a heart ventricular assist device (HVAD) induced ventricular arrythmia and the processing circuitry is further configured to determine a risk of the HVAD induced ventricular arrythmia occurring in the patient is high in response to the determined difference of patient metric (h) meeting a respective HVAD induced ventricular arrythmia risk threshold.

Example 13: A method includes obtaining one or more measurement values of one or more patient metrics of a patient; determining a baseline value for each of the respective one or more patient metrics based on measurement values of the one or more patient metrics over a first period of time; determining a short-term value for each of the one or more patient metrics based on measurement values of the one or more patient metrics over a second period of time, the second period of time being shorter than the first period of time; determining a difference between each of the short-term values and the respective baseline value for each of the one or more patient metrics; determining that a risk of an adverse event occurring in the patient is high in response to the determined difference of at least one patient metric of the one or more patient metrics meeting a respective adverse event risk threshold or in response to an accumulated value of the determined differences for each of the one or more metrics meeting a respective accumulated adverse event risk threshold; and generating for output an adverse event high risk alert in response to determining the patient has the high risk of the adverse event occurring.

Example 14: The method of example 13, wherein the one or more patient metrics comprise at least one of (a) heart rate during a day time period; (b) heart rate during a night time period; (c) percent atrial pacing; (d) percent ventricular pacing; (e) heart rate variability; (f) activity; (g) daily intrathoracic impedance; or (h) ventricular tachycardia or ventricular fibrillation status.

Example 15: The method of example 14, further comprising applying a long-term filter to the measurement values of each of the one or more patient metrics over the first period of time to determine the baseline value for each of the respective one or more patient metrics.

Example 16: The method of example 15, further comprising applying a short-term filter to the measurement values of each of the one or more patient metrics over the second period of time to determine the short-term value for each of the respective one or more patient metrics.

Example 17: The method of example 16, wherein the long-term filter is a moving average filter applied over the first period of time and the short-term filter is a moving average filter applied over the second period of time.

Example 18: The method of any of examples 14 through 17, wherein the adverse event is a thrombus and the method further comprising determining a risk of the thrombus occurring in the patient is high in response to the determined difference of at least one patient metric of patient metrics (a)-(g) meeting a respective thrombus risk threshold or in response to an accumulated value of the determined differences for each of the patient metrics (a)-(g) meeting a respective accumulated thrombus risk threshold.

Example 19: The method of any of examples 14 through 18, wherein the adverse event is a stroke and the method further comprising determining a risk of the stroke occurring in the patient is high in response to the determined difference of at least one patient metric of patient metrics (a)-(e) meeting a respective a stroke risk threshold or in response to an accumulated value of the determined differences for each of the patient metrics (a)-(e) meeting a respective accumulated stroke risk threshold.

Example 20: The method of any of examples 14 through 19, wherein the adverse event is a heart ventricular assist device (HVAD) induced ventricular arrythmia and the method further comprising determining a risk of the HVAD induced ventricular arrythmia occurring in the patient is high in response to the determined difference of patient metric (h) meeting a respective HVAD induced ventricular arrythmia risk threshold.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system comprising:
an implantable blood pump of an implantable medical device, the implantable medical device configured to receive a plurality of sensed physiological signals indicative of a plurality of cardiovascular parameters of a patient, and to collect and store measurement values of one or more patient metrics of the patient corresponding to the cardiovascular parameters and based on the received plurality of physiological signals;

the implantable medical device comprising processing circuitry configured to:
determine a baseline value for each of the respective one or more patient metrics based on measurement values of the one or more patient metrics over a first period of time;
determine a short-term value for each of the one or more patient metrics based on measurement values of the one or more patient metrics over a second period of time, the second period of time being shorter in duration than the first period of time;
determine a difference between each of the short-term values and the respective baseline value for each of the one or more patient metrics;
determine that a risk of an adverse event occurring in the patient is high in response to the determined difference of at least one patient metric of the one or more patient metrics meeting a respective adverse event risk threshold or in response to an accumulated value of the determined differences for each of the one or more patient metrics meeting a respective accumulated adverse event risk threshold;
wherein the adverse event is a high risk of an occurrence of a stroke based on a determination using a first set of the one or more patient metrics or wherein the adverse event is a high risk of an occurrence of a thrombus based on a determination using a second set of the one or more patient metrics that is different from the first set of the one or more patient metrics; and
generate for output an adverse event high risk alert in response to determining the patient has the high risk of the adverse event occurring.

2. The system of claim 1, wherein the one or more patient metrics comprise at least one of (a) heart rate during a day time period; (b) heart rate during a night time period; (c) percent atrial pacing; (d) percent ventricular pacing; (e) heart rate variability; (f) a patient activity level; (g) daily intrathoracic impedance; or (h) ventricular tachycardia or ventricular fibrillation status.

3. The system of claim 2, wherein the processing circuitry is further configured to apply a long-term filter to the measurement values of each of the one or more patient metrics over the first period of time to determine the baseline value for each of the respective one or more patient metrics.

4. The system of claim 3, wherein the processing circuitry is further configured to apply a short-term filter to the measurement values of each of the one or more patient metrics over the second period of time to determine the short-term value for each of the respective one or more patient metrics.

5. The system of claim 4, wherein the first period of time is 6 months, and the second period of time is 30 days.

6. The method of claim 4, wherein the long-term filter is a moving average filter applied over the first period of time.

7. The system of claim 4, wherein the short-term filter is a moving average filter applied over the second period of time.

8. The system of claim 2, wherein the processing circuitry is further configured to determine that the risk of the thrombus occurring in the patient is high in response to the determined difference of at least one patient metric of patient metrics (a)-(g) meeting a respective thrombus risk threshold or in response to an accumulated value of the determined differences for each of the patient metrics (a)-(g) meeting a respective accumulated thrombus risk threshold.

9. The system of claim 2, wherein the processing circuitry is further configured to determine that the risk of the stroke occurring in the patient is high in response to the determined difference of at least one patient metric of patient metrics (a)-(e) meeting a respective stroke risk threshold or in response to an accumulated value of the determined differences for each of the patient metrics (a)-(e) meeting a respective accumulated stroke risk threshold.

10. The system of claim 2, wherein the adverse event is a heart ventricular assist device (HVAD) induced ventricular arrythmia and the processing circuitry is further configured to determine a risk of the HVAD induced ventricular arryth- mia occurring in the patient is high in response to the determined difference of patient metric (h) meeting a respec- tive HVAD induced ventricular arrythmia risk threshold.

11. The system of claim 1, wherein the adverse event is a heart ventricular assist device (HVAD) induced ventricular arrythmia.

12. The system of claim 1, wherein the generated adverse event high risk alert is to cause a medical intervention to be performed on the patient.

13. A method comprising:

receiving, at a system comprising an implanted blood pump of an implantable medical device implanted in a patient, a plurality of sensed physiological signals, the sensed physiological signals indicative of measurement values of one or more patient metrics of the patient corresponding to a set of cardiovascular parameters of the patient;

performing, using processing circuitry included in the implantable medical device, the method further com- prising:

determining a baseline value for each of the respect on or more patient metrics based on measurement val- ues of the one or more patient metrics over a first period of time;

determining a short-term value for each of the one or more patient metrics based on measurement values of the one or more patient metrics over a second period of time, the second period of time being shorter than the first period of time;

determining a difference between each of the short- term values and the respective baseline value for each of the one or more patient metrics;

determining that a risk of an adverse event occurring in the patient is high in response to the determined difference of at least one patient metric of the one or more patient metrics meeting a respective adverse event risk threshold or in response to an accumulated value of the determined differences for each of the one or more metrics meeting a respective accumu- lated adverse event risk threshold;

wherein the adverse event is a high risk of an occur- rence of a stroke based on a determination using a first set of the one or more patient metrics or wherein the adverse event is a high risk of an occurrence of a thrombus based on a determination using a second set of the one or more patient metrics that is different from the first set of the one or more patient metrics; and generating for output an adverse event high risk alert in response to determining the patient has the high risk of the adverse event occurring.

14. The method of claim 13, wherein the one or more patient metrics comprise at least one of (a) heart rate during a day time period; (b) heart rate during a night time period; (c) percent atrial pacing; (d) percent ventricular pacing; (e) heart rate variability; (f) a patient activity level; (g) daily intrathoracic impedance; or (h) ventricular tachycardia or ventricular fibrillation status.

15. The method of claim 14, further comprising applying a long-term filter to the measurement values of each of the one or more patient metrics over the first period of time to determine the baseline value for each of the respective one or more patient metrics.

16. The method of claim 15, further comprising applying a short-term filter to the measurement values of each of the one or more patient metrics over the second period of time to determine the short-term value for each of the respective one or more patient metrics.

17. The method of claim 16, wherein the long-term filter is a moving average filter applied over the first period of time and the short-term filter is a moving average filter applied over the second period of time.

18. The method of claim 14, the method further compris- ing determining a risk of the thrombus occurring in the patient is high in response to the determined difference of at least one patient metric of patient metrics (a)-(g) meeting a respective thrombus risk threshold or in response to an accumulated value of the determined differences for each of the patient metrics (a)-(g) meeting a respective accumulated thrombus risk threshold.

19. The method of claim 14, the method further compris- ing determining a risk of the stroke occurring in the patient is high in response to the determined difference of at least one patient metric of patient metrics (a)-(e) meeting a respective a stroke risk threshold or in response to an accumulated value of the determined differences for each of the patient metrics (a)-(e) meeting a respective accumulated stroke risk threshold.

20. The method of claim 14, wherein the adverse event is a heart ventricular assist device (HVAD) induced ventricular arrythmia and the method further comprising determining a risk of the HVAD induced ventricular arrythmia occurring in the patient is high in response to the determined difference of patient metric (h) meeting a respective HVAD induced ventricular arrythmia risk threshold.

* * * * *